United States Patent
Li et al.

(10) Patent No.: US 8,024,277 B2
(45) Date of Patent: Sep. 20, 2011

(54) RECONSTRUCTION OF GENE NETWORKS AND CALCULATING JOINT PROBABILITY DENSITY USING TIME-SERIES MICROARRAY, AND A DOWNHILL SIMPLEX METHOD

(75) Inventors: Sai-Ping Li, Taipei (TW); Sun-Chong Wang, Taipei (TW)

(73) Assignee: Academia Sinica, Taipei (TW)

( * ) Notice: Subject to any disclaimer, the term of this patent is extended or adjusted under 35 U.S.C. 154(b) by 779 days.

(21) Appl. No.: 12/131,162

(22) Filed: Jun. 2, 2008

(65) Prior Publication Data
US 2009/0063376 A1    Mar. 5, 2009

Related U.S. Application Data

(63) Continuation-in-part of application No. 10/847,094, filed on May 16, 2004, now abandoned.

(51) Int. Cl.
*G06F 17/00* (2006.01)
(52) U.S. Cl. .......................................................... 706/45
(58) Field of Classification Search .............. 706/45–48, 706/62; 702/19–20
See application file for complete search history.

(56) References Cited

U.S. PATENT DOCUMENTS
2007/0276610 A1* 11/2007 Korenberg ...................... 702/19

OTHER PUBLICATIONS

Stricker et al., Linkage Analysis With an Alternative FOrmulation for the Mixed Model of Inheritance: The Finite Polygenic Mixed Model, 1995, Genetics 141: 1651-1656.*
Manana et al., A Grid Computing Approach to Subtraction Radiography, 2006, IEEE ICIP, pp. 3325-3328.*

\* cited by examiner

*Primary Examiner* — David Vincent
(74) *Attorney, Agent, or Firm* — Venable LLP; Jeffri A. Kaminski

(57) ABSTRACT

Gene regulation network is reconstructed using time series microarray data under the method of the Bayesian network. Particular power-law function is used to calculate the joint probabilities among genes across time points. This invention discloses the use of the downhill simplex algorithm to find global maxima of interrelational likelihood. Arcs with higher frequencies are selected to establish the gene regulation network. Prior knowledge may be included into candidate gene networks to accelerate search for best networks.

7 Claims, 8 Drawing Sheets

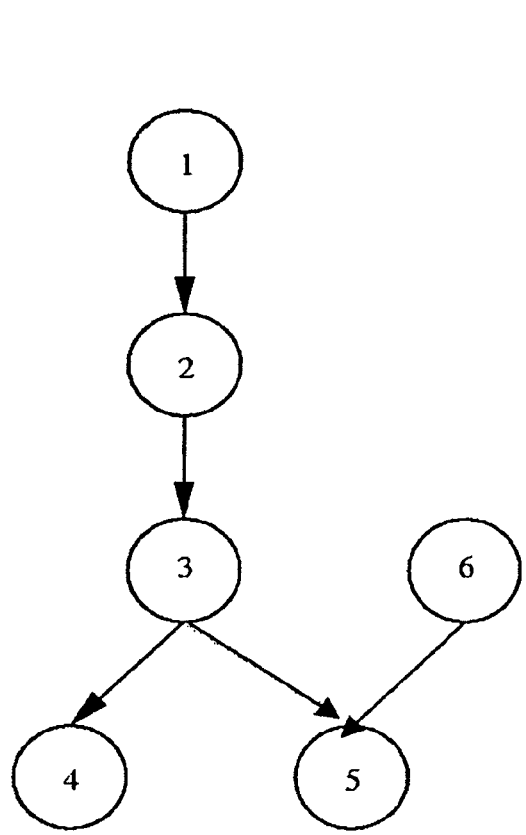
Fig. 4A
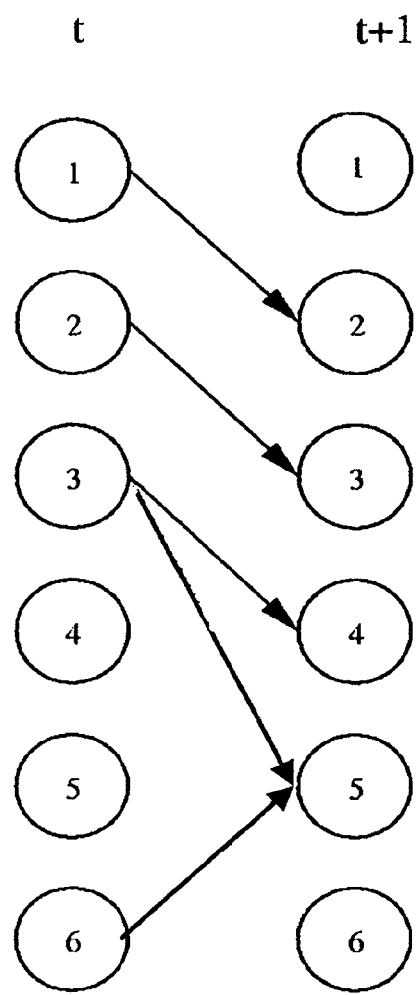
Fig. 4B
Fig. 4

RECONSTRUCTION OF GENE NETWORKS AND CALCULATING JOINT PROBABILITY DENSITY USING TIME-SERIES MICROARRAY, AND A DOWNHILL SIMPLEX METHOD

CROSS-REFERENCE TO RELATED APPLICATION

This application is a continuation-in-part of U.S. application Ser. No. 10/847,094, filed May 16, 2004 now abandoned, the entire disclosure of which is hereby incorporated by reference herein.

FIELD OF THE INVENTION

The present invention relates to analysis of causal relationships using time-series data, especially to its application in the reconstruction of gene regulation networks using time-series microarray data.

BACKGROUND OF THE INVENTION

With the advent of DNA microarray technology, researchers can now measure the expression levels of all genes of an organism in a single assay. Measurements have since been carried out to observe the state of cells undergoing developmental program or subjected to experimental/environmental stimuli. Analysis of microarray data by clustering methods has become popular. In the analysis, patterns of gene expressions across time points or different treatments are grouped into clusters. The function of an unknown gene can then be inferred from that of the known genes in the same cluster.

Although cells of the same species carry the same genetic blueprint in the DNA, not all genes express particular features at any given time and what are expressed are always at different levels. Gene products, mainly proteins, run or catalyze the biochemical reactions in living organisms. When and to what extent a gene is regulated by other genes are keys to understand the life. A step beyond clustering is therefore to reconstruct gene regulation networks. Several methods for gene network modeling and reconstruction were thus published.

Simon et al. demonstrated, using the genome-wide transcription factor binding site analysis, the serial regulation of transcription factors during a yeast cell cycle. See Simon et al., "Serial regulation of transcription regulators in the yeast cell cycle," Cell, 106 (2001) 697-708. By serial regulation, it was meant that the transcription activators that function during one stage of the cell cycle regulate the transcription activators/cyclin genes that function during the next stage. In FIG. 4B of their paper is shown such a serial regulatory network. Qian et al. disclosed a technology to use an SVM machine learning approach to reconstructing the cell-cycle gene network. See: Qian et al., "Prediction of regulatory networks: genome-wide identification of transcription factor targets from gene expression data," Bioinformatics, Vol. 19 no. 15 2003, pages 1917-1926. Jansen et al. disclosed a technology to reconstruct a cell-cycle gene network using a database. See: Jasen et al., "A Bayesian Networks Approach for Predicting Protein-Protein Interactions from Genomic Data," Science, Vol. 302, 17 Oct. 2003, p. 449-453. These inventions rely heavily on databases although they also resorted to Bayesian networks. Both require extensive learning before application. In general, in the computational science, good learning depends on informative databases in which answers are buried. New features that are not included in the database cannot be discovered in the machine learning technology. In the case of gene or protein networks, databases with large number of data do not exist and quality of the regulatory relations in the databases is poor. These facts made it difficult to use the machine learning approach in the reconstruction of gene networks. Furthermore, in analyzing the data, a plurality of ad hoc parameters such as thresholds, likelihood cuts etc. are necessary. Interpretation of the data depends deeply on the values of the parameters as selected.

It is thus necessary to provide an innovative method for reconstruction of gene networks from existing noisy data.

It is also necessary to provide a method for reconstruction of gene networks, the levels of detail of the reconstructed gene networks being inversely proportional to the noisiness of the data.

It is also necessary to provide a method for reconstruction of gene networks using a computation-oriented approach.

It is also necessary to provide a method for the reconstruction of gene networks with low false positive rate.

It is also necessary to provide a method for reconstruction of gene networks wherein no ad hoc parameters are necessary.

It is also necessary to provide a method for reconstruction of gene networks from time-series microarray data.

It is also necessary to provide a device for reconstruction of gene networks using all the above methods.

OBJECTIVES OF THE INVENTION

The objective of this invention is to provide a novel method for reconstruction of gene networks from noisy data.

Another objective of this invention is to provide a method for reconstruction of gene networks whose levels of detail are inversely proportional to the noise levels of the data.

Another objective of this invention is to provide a method for reconstruction of gene networks using a computation-oriented approach.

Another objective of this invention is to provide a method for reconstruction of gene networks wherein no ad hoc parameters are necessary.

Another objective of this invention is to provide a method for reconstruction of gene networks from time-series microarray data.

Another objective of this invention is to provide a device for reconstruction of gene network using all the above methods.

SUMMARY OF THE INVENTION

According to this invention, a method for reconstruction of yeast cell-cycle gene network from time series microarray data is disclosed. The method of this invention is used to reconstruct gene regulation networks and comprises the following steps:

obtaining a time-series microarray dataset of gene expression ratios relating to a set of genes;

generating from a computer tool a first predetermined amount of gene regulation network templates as candidate networks, each candidate network structure being represented by an integer array for genetic algorithm operations;

fitting data of said dataset into said candidate networks by downhill simplex method;

calculating joint probability density (score) of a candidate network obtained from said fitting, S, according to the following equation, respectively:

$$\text{score}(S) = \log(P(x \mid S, \hat{\Theta})) - \frac{d}{2}\log(R \cdot n \cdot (T-1))$$

wherein score(S) approximates the logarithm of the joint probability density of a candidate network, S, and the parameters, $\hat{\Theta}$, represent the parameters that maximize the likelihood function $P(x|S, \Theta)$, wherein:

$$P(x \mid S, \Theta) = \prod_{t=1}^{T-1} \prod_{i=1}^{n} p(x_i, t; \theta_i), \quad (4)$$

wherein $p(x_i, t; \theta_i)$ represents conditional probability density of the expression of any gene i in said candidate network at time t, relatively to parameters $\theta_i$, and $\Theta$ is the cell containing parameters $\theta_i$, and $x_i$ is the measured expression ratio of gene i and is non-negative real; wherein:

$$p(x_i, t+1; \theta_i) = N\left(x_i(t+1) - \alpha_i \prod_j x_j(t)^{\omega_{ji}} - (1-\beta_i)x_i(t), \delta^2\right)$$

wherein exponent, $\omega_{ji}$, is real, wherein, when $\omega_{ji}$ is positive (negative), gene j induces (represses) the expression of gene i and $\alpha_i$ and $\beta_i$ are both positive constants, quantifying the rate of transcription and degradation, respectively, $$x_i(t+1) = \alpha_i \prod_j x_j(t)^{\omega_{ji}} + (1-\beta_i)x_i(t) + \varepsilon_i(t)$$

wherein $\varepsilon_i(t)$ is the measurement error for gene i at time t, $\delta^2$ is the variance of a Gaussian distribution representing said errors, $\varepsilon_i(t)$; and $$\frac{d}{2}\log(R \cdot n \cdot (T-1))$$

is a penalty against structure complexity, d equals to the number of parameters in said candidate network n represents number of genes included in said fitted candidate networks, T represents number of microarray measurements performed at time points 0, 1, ..., and T−1, and R represents number of repeats of said measurement;

selecting from said candidate networks a second predetermined number of candidate networks with the highest score values;

mating and mutating said selected candidate networks according to genetic algorithms to generate candidate networks of offspring generation;

fitting data of said dataset into said networks of offspring generation and calculating score values of said networks of offspring generation;

determining whether the average of the obtained score values reach a plateau;

if not, the steps of said mating and mutating and said score calculation are repeated;

otherwise, a third predetermined number of candidate networks with higher score values obtained from said calculation after fitting are selected; and frequency of existence of arcs in candidate networks selected in the previous step is calculated;

ranking arcs according to existence frequency and selecting arcs of high existence frequency;

reconstructing gene network using said selected arcs and related genes; and outputting result of said reconstruction.

These and other objectives and advantages of this invention may be clearly understood from the detailed description by referring to the following drawings.

BRIEF DESCRIPTION OF THE DRAWINGS

FIGS. 4a and 4b show the structure of a gene regulation network consisting of 6 genes and 5 arcs. FIG. 4a shows its nodes and arcs and FIG. 4b shows its time information.

DETAILED DESCRIPTION OF THE INVENTION

Figure 1:
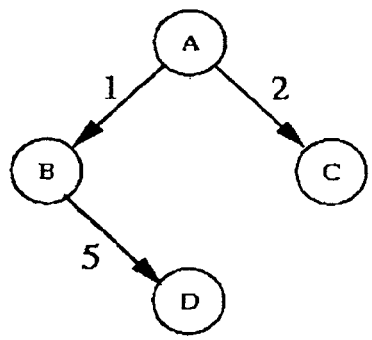
FIG. 1 shows the representation of the network structure and the cross-over operation in the genetic algorithm.
Figure 1:
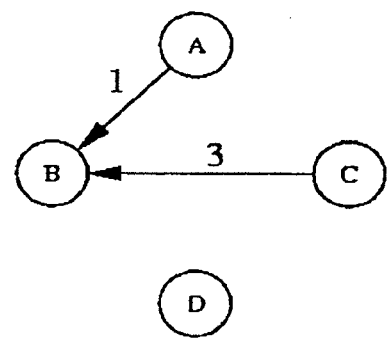
Figure 1:
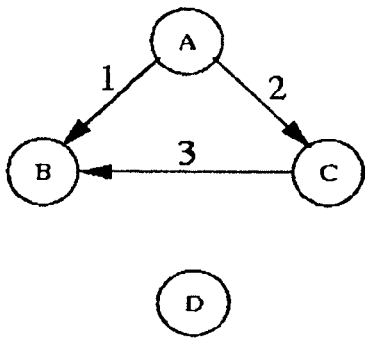
Figure 1:
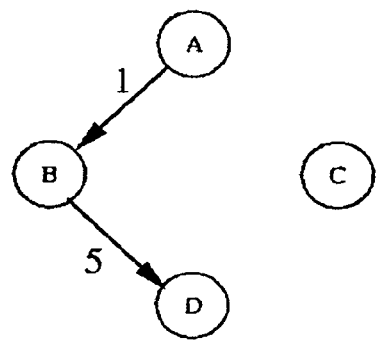

The task of gene network reconstruction is to find the structure, together with the appropriate parameters in it whose joint probability density is maximal. A system to reconstruct the gene regulation network shall provide a function to describe and to estimate the regulatory relations between and among gene expressions.

Events of gene expression are stochastic. Microarray technology in its infancy incurs substantial noise. Because of the cost, replications in typical microarray experiments remain low. Methodologies to reconstruct gene regulation networks should therefore bear rich statistics and probability semantics. It is found that a graph-based method called Bayesian network (BN), well developed in the filed of uncertainty and artificial intelligence, suits most of the requirements. It is thus possible to use a Bayesian network to reconstruct a gene regulation network.

Bayesian Network (BN)

A BN consists of nodes and arcs. In using a BN to represent the gene regulation network, the node represents the genes under observation. The value of each node, a random variable, gives the expression ratio of a particular gene. The existence of an arc between two nodes establishes a probabilistic dependence in expression between them. Given a model of gene regulation, the conditional probability density for an arc can be described. With such a structure, namely the arcs and the linked nodes, the joint probability density of the measured gene expression data can be obtained as a product of the conditional probability densities.

In contrast to previous works, wherein gene expression ratios are treated as discrete variables, the present invention treats gene expression ratios as continuous variables in the BN, so that no information is lost in decartelization. Moreover, the model of gene regulation as disclosed in this invention is a non-linear function which relates the transcription rate of a regulated gene to the expression ratios of the regulatory genes. In the embodiment of this invention, the function comprises a power law function. This power law model, having roots in biochemistry, exhibits generality and robustness in the application. In this invention the model is applied to include delayed transcriptions, which can arise due to transport of gene products across cellular compartments.

The BN is then developed for time series gene expression data. Instead of the EM (estimation maximization) algorithm in most BN implementations of the prior art, this invention discloses the use of the downhill simplex algorithm to find global maxima of interrelations.

Power Law Function

In a microarray assay, treated and wild samples are usually labeled with red and green fluorescein respectively. The background-subtracted intensity of the emitted light reflects the abundance of the mRNA in the sample mixture. The ratio of the red to green intensity indicates the degree of up or down regulation of the gene upon treatment. Rate of gene transcription may be modeled by the following equation:

$$\frac{dx_i}{dt} = \alpha_i \prod_j x_j^{\omega_{ji}} - \beta_i x_i \quad (1)$$

wherein $x_i$ is the measured expression ratio of gene i and is non-negative real. $\alpha_i$ and $\beta_i$ are both positive constants, quantifying the rate of transcription and degradation, respectively. The product is ever the set of genes that have arcs pointing to gene i. The exponent, $\omega_{ji}$, is real. When $\omega_{ji}$ is positive (negative), gene j induces (represses) the expression of gene i.

This multivariate power law function was coined S-system and has been extensively used in chemical and biochemical kinetics. It was shown that any non-linear function can be locally represented by the power law form if the function is logarithmically differentiable.

Since microarray measurements are conducted at discrete time points, the model can be written in the discrete form:

$$x_i(t+1) = \alpha_i \prod_j x_j(t)^{\omega_{ji}} + (1 - \beta_i) x_i(t) + \varepsilon_i(t) \quad (2)$$

wherein $\varepsilon_i(t)$ is the measurement error for gene i at time t. For simplicity, it is reasonable to assume in the rest of this specification that the errors, $\varepsilon_i(t)$'s, are Gaussian distributed with mean zero and variance, $\delta^2$, common to all genes at all time points: $\varepsilon_i(t) = \varepsilon = N(0, \delta^2)$ for any i and any t where $N(0, \delta^2)$ is the Gaussian distribution function with mean 0 and variance $\delta^2$.

Once a candidate structure of the gene regulation network is given, the conditional probability density, $p(x_i, t+1; \theta_i)$, of the expression of any gene i in the network at time t+1 can be readily written down as follows, apart from the prior probability distributions on the $\alpha_i$, $\beta_i$, $\omega_{ji}$, and $\delta$, which are assumed to be uniform, $$p(x_i, t+1; \theta_i) \equiv p(x_i, t+1; \alpha_i, \beta_i, \omega_{ji}) \quad (3)$$
$$= N\left(x_i(t+1) - \alpha_i \prod_j x_j(t)^{\omega_{ji}} - (1 - \beta_i) x_i(t), \delta^2\right)$$
$$= \varepsilon_i(t)$$
$$= \varepsilon.$$

The joint probability density, $P(x|S,\Theta)$, of the candidate network of structure, S, and parameters, $\Theta = \{\theta_i\}$, becomes:

$$P(x | S, \Theta) = \prod_{t=1}^{T-1} \prod_{i=1}^{n} p(x_i, t; \theta_i), \quad (4)$$

wherein n genes are included in the network and T microarray measurements are performed at time points 0, 1, ..., and T−1. If the series of measurements is repeated R times, the probability density for each replicate is multiplied to obtain the final joint probability density. To avoid bias, integration of $P(x|S, \Theta)$ over the parameters $\alpha_i$'s, $\beta_i$'s, $\omega_{ji}$'s and $\delta$ with their prior distributions is preferably carried out. This marginalization can prove to be intractable and the approximation that approaches the logarithm of the likelihood may be employed, as long as the quantity $R \times n \times (T-1)$ is large enough. So we have:

$$\text{score}(S) = \log\left(P(x | S, \hat{\Theta})\right) - \frac{d}{2} \log(R \cdot n \cdot (T-1)) \quad (5)$$

wherein $\hat{\Theta}$ represents the values of the parameters $\Theta$ that maximize the likelihood function $P(x|S,\Theta)$, and the second term, with d equal to the number of parameters in the structure, is a penalty against structure complexity. The first term of the score metric is simply the minimum of the sum of squared prediction errors, plus a constant depending on $\delta$.

The task of the gene regulation network reconstruction, together with the embedded parameters, is to search for the structure that scores highest. The advantage of the above score function is that parsimonious structures that fit the data well can be found.

Genetic Algorithms

There are two disparate types of unknowns in the above Bayesian network approach.

One is the possible combinations of arcs between genes across time points. The other is the real-values of $\alpha$'s, $\beta$'s and $\omega$'s in the arcs. The expression level of a gene at present time may be affected by the expression levels of any genes at the previous time point. Given n genes, there can thus be n×n arcs across time points t and t+1 and the number of possible network structures amounts to $2^{n \times n}$. If 10 genes are involved, there can be $10^{30}$ possible network structures to be analyzed. As n increases, the number of possible structures explodes. An exhaustive search in the structure space cannot be practical.

Although it is not intended to limit the scope of this invention, in the present invention a genetic algorithm (GA) is employed to explore the structure space. Inspired by Darwinian evolution and applying Mendelian genetics, computational researchers represent possible solutions to optimization problems by numerical arrays called 'chromosomes'.

The chromosomes are then crossed over and mutated. Fitter chromosomes are selected for next generation. The process is repeated until convergence.

FIG. 1 shows the GA representation of a network structure and the cross-over operation between two parents. In the representation, different arcs have their own unique integer numbers in the population of the candidate networks. The top two parents are represented by integer arrays (1, 2, 5) and (1, 3) respectively. Nodes represent genes and arcs regulatory relations. In crossing-over, if the last element of the two arrays are chosen to swap, the offspring arrays become (1, 2, 3) and (1, 5) as shown in the bottom two networks. A gene network is therefore conveniently encoded by an integer array in this invention. Mutation is on individual networks.

Figure 2:
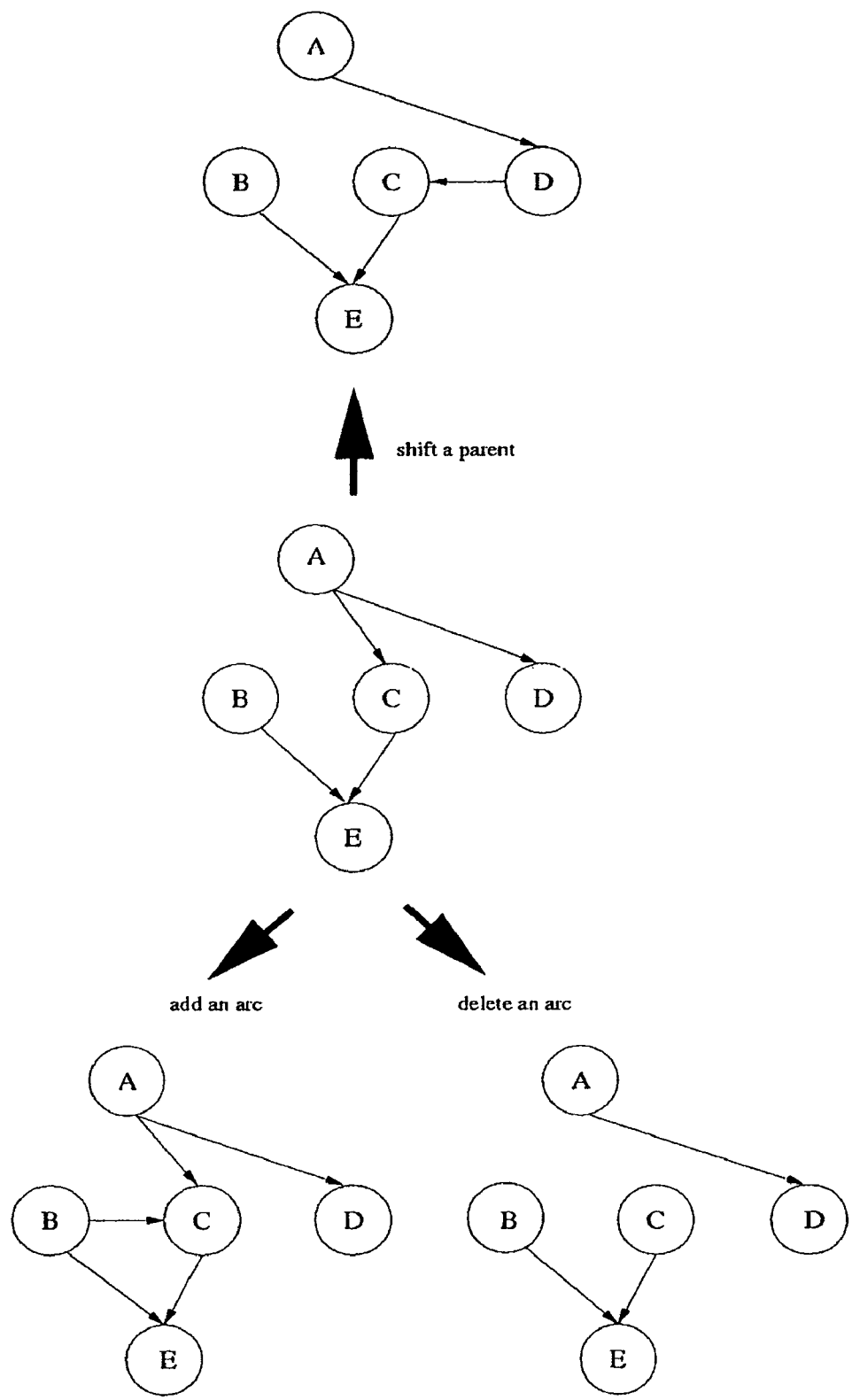
FIG. 2 shows the mutation operations of the genetic algorithm.

Three types of mutations are defined in this invention. They are: adding a new arc to a target gene; deleting an existing arc to a target gene; and changing the parent gene of an existing arc. FIG. 2 shows these mutation operations. An offspring network descends from the parent by adding a new arc, deleting an existing arc, or shifting the parent gene of an existing arc in the parent network. The three mutation operations have equal chances of being applied to a structure. In the GA, first of all, a population of candidate networks is established. Their scores are calculated according to Equation (5) and the networks are ranked. Networks with higher scores are selected as parents. Cross-over operations are then applied to some pairs of the parents. Mutation operations are performed on the rest of the parents. A new generation of population is thus obtained. The procedure is iterated until the average network score of the population reaches a plateau.

When evaluating the score of a candidate network during the ranking process in the GA, the parameter values that minimize the sum of squared prediction errors, by the downhill simplex method for multidimensional function minimization, can be found. A simplex in d-dimension is a polyhedron of d+1 vertexes. In the method, a vertex stores a set of possible parameter values, and the polyhedron, mimicking moves of an amoeba, crawls around the parameter space, creeping down valleys and shrinking its size down to the bottom of narrow valleys. We found the downhill simplex algorithm effective in minimizing the sum of squared prediction errors of the power-law form in Equation (5).

In the present invention, a network structure is encoded in an integer array, as mentioned above. The size of the array is variable depending on the number of arcs present in the network. Given a structure (genotype), the set of the associated parameters is mapped according to the model of Equations (1)-(4). Learning of the optimal parameter values (phenotype) is performed by the downhill simplex method. After learning, the optimal values are stored in the arcs (and nodes) which continue to evolve in the GA. A network starts with only one arc in the first generation of the GA. Arcs can be either created or deleted during evolution. The exponent ω is initialized to zero in any newly created arc. Since the evolutionary operations are on the structure and the optimization is on the parameter values which are inscribed in the structure after learning, the implemented GA is Lamarckian. It is shown that a Lamarckian GA is more efficient in problems with high dimensionality than pure GA alone. An arc survives only if its benefit (the first term in the score metric) outweighs the penalty (second term in the score). In a typical fitting problem, as the fitting function gets more complicated, the fitting error (sum of squared prediction errors) gets smaller. In the score function of Equation (5), when the fitting error decreases, the first term approaches an asymptotic value that is set by δ. Further growth of the network structure will be penalized by the second term of the score function. A feature of this invention is thus that networks grow in complexity up to a point that is determined by the noise level of the microarray experiment. The feature results from a sound statistical modeling of the problem, waiving otherwise ad hoc parameter settings.

Another important advantage of adopting the GA is that a significance or confidence metric can be readily defined and applied at the end of the GA search. The last generation of the GA contains a population of candidate networks that score very high. The candidate networks whose scores differ by only a fraction should be considered as competitive due to the low replicate and high noise of microarray data. It is reckless to report the highest scoring network as the solution. Instead, the frequencies of arcs that appear in the candidate networks in the last generation of the GA are calculated. If the arc pointing from gene i to gene k is present in 90% of the networks while the arc from gene j to gene k appears in only 10% of the networks, then i→k is more significant than j→k is concluded.

Another feature of the present invention is that prior knowledge can be incorporated to help GA search. For example, if it is known from biologists (or from previous analyses) that gene i regulates gene j, we hardcode arcs i→j in the initial population of the GA. In this way, as knowledge accumulates, the reconstructed networks may be expanded from subnetworks to networks, from networks for a particular biological process to networks for multiple biological processes, etc.

Reconstruction of Gene Network

Figure 3:
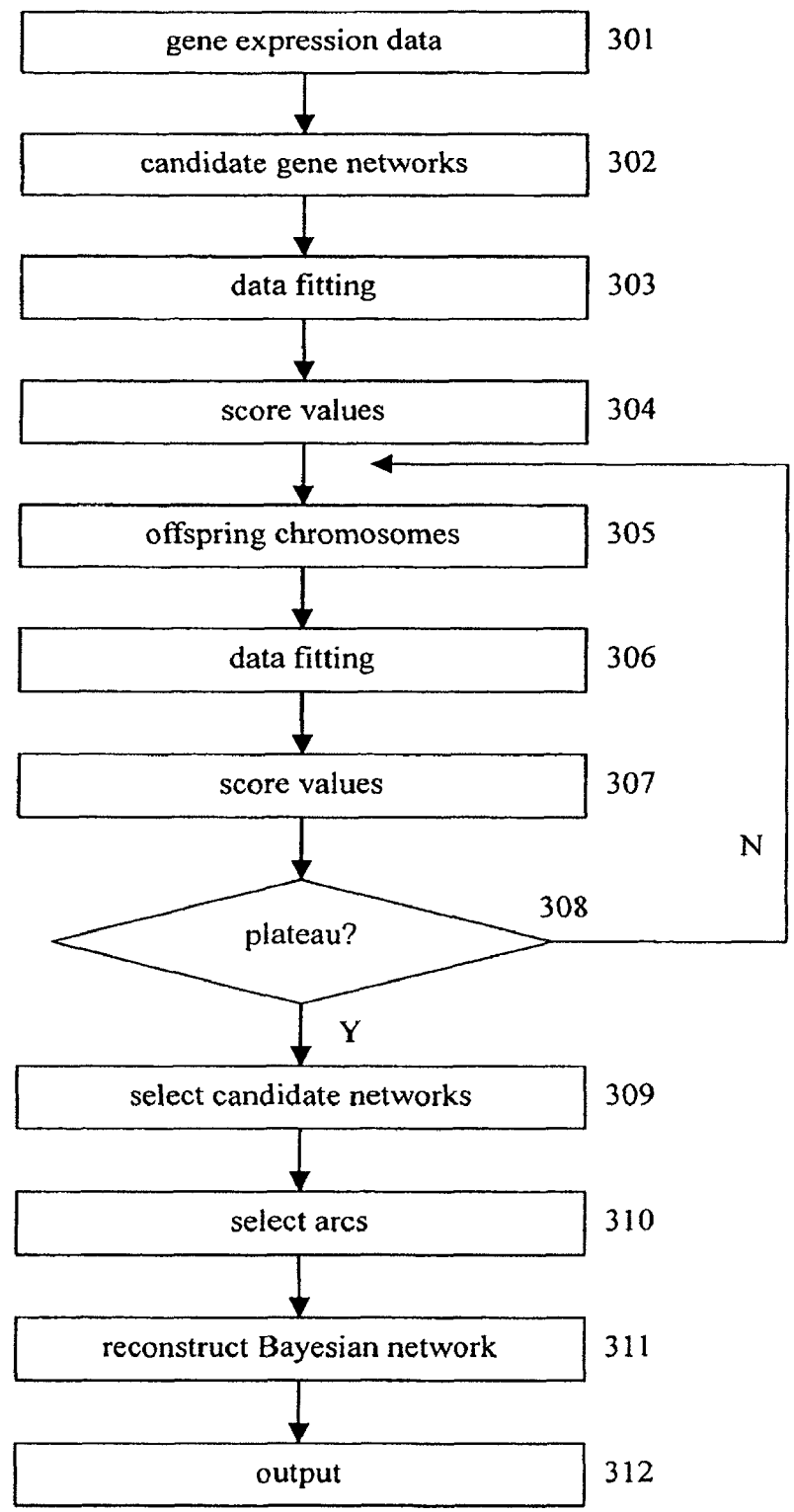
FIG. 3 shows the flow diagram of the method for reconstructing gene networks from time series microarray data of this invention.

FIG. 3 shows the flowchart of the method for reconstruction of gene networks from time series data of this invention. As shown in this figure, in using the invented method to reconstruct a gene regulation network, at 301a microarray dataset of gene expression in T time points, called time series data, is obtained. At 302 a certain number of candidate gene networks are randomly generated by a computerized tool. At 303 data of the time series data are fitted to the candidate gene networks. A network is expressed by an array of integers in the genetic algorithm. At 304 the score values of all candidate networks are calculated according to Equation (5).

At 305 a predetermined number of candidate networks is selected from those with higher score values and mate the selected candidate networks according to the genetic algorithm to generate offspring chromosomes. At 306 the time series data are fitted into the offspring chromosomes and, at 307, the score values of the offspring candidate networks are calculated according to Equation (5) again. At 308 determine whether the average value of the score values reaches a plateau. If not, the process returns to step 305 and steps 304-307 are repeated; otherwise, a predetermined number of candidate networks with higher score values are selected to calculate the frequency of arcs existing in these candidate networks at 309. At 310 arcs are ranked according to their frequencies and arcs with high frequency values are selected as basis of reconstruction of gene networks. At 311a gene network is established according the arcs selected in the previous step. At 312 the result is output.

Simulation

The development of the present invention is aided by simulation. FIGS. 4a and 4b show the structure of a gene regulation network consisting of 6 genes and 5 arcs. FIG. 4a shows its nodes and arcs and FIG. 4b shows its time information. The parameters in the structure are shown below:

$$x'_1 - x_1 = -0.2 x_1$$

$$x'_2 - x_2 = 1.2 x_1^{2.0} - 0.6 x_2$$

$$x'_3 - x_3 = 1.3 x_2^{0.5} - 0.7 x_3$$

$$x'_4 - x_4 = 1.8 x_3^{1.0} - 1.5 x_4$$

$$x'_5 - x_5 = 2.0 x_3^{-2.0} x_6^{-0.5} - 1.0 x_5$$

$$x'_6 - x_6 = -0.1 x_6 \quad (6)$$

where $x'_i$ and $x_i$ are the expression ratios of gene i at the next and present time points, respectively. It is assumed that $x_i$'s are measured at 7 equally spaced time points and that $x_i(0)=1$ for all i. The goal now is to reconstruct by establishing the structure (5 arcs) and the 15 associated parameters (5 ω's, 4 α's and 6 β's) from the 36 (6 genes*7−1 time points) data points, assuming the dynamic model of Equation (2). Note that for a fully connected network, there need to be 36 ω's+6 α's+6 β's=48 parameters. With only 36 data points the solution is under-determined. This highlights the difficulty with other conventional approaches. The evolution starts with each candidate network having only one arc. An initial network tries to fit the 36 data points with only 1 ω+1 α+6 β's=8 parameters. As the networks evolve, more arcs, and thus more parameters, emerge to fit the data until the score/arcs stop increasing.

Figure 5A:
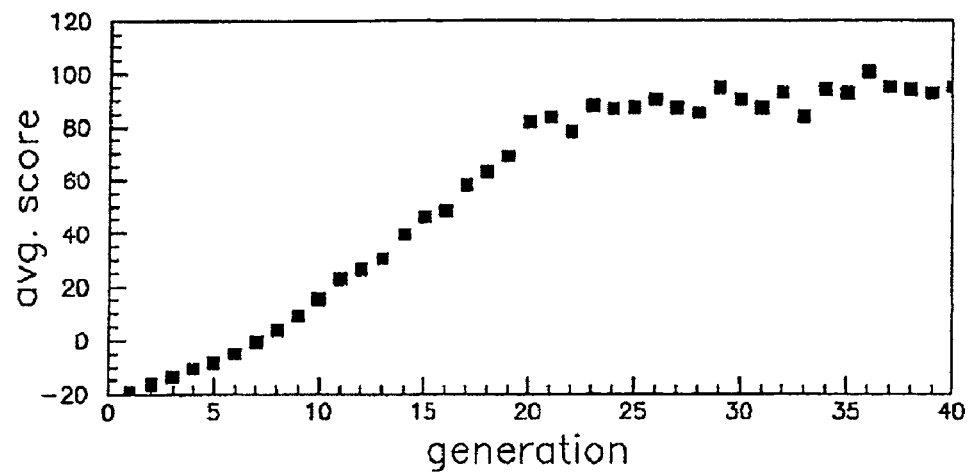
FIG. 5a shows the increase in the average score as the iteration is conducted.
Figure 5B:
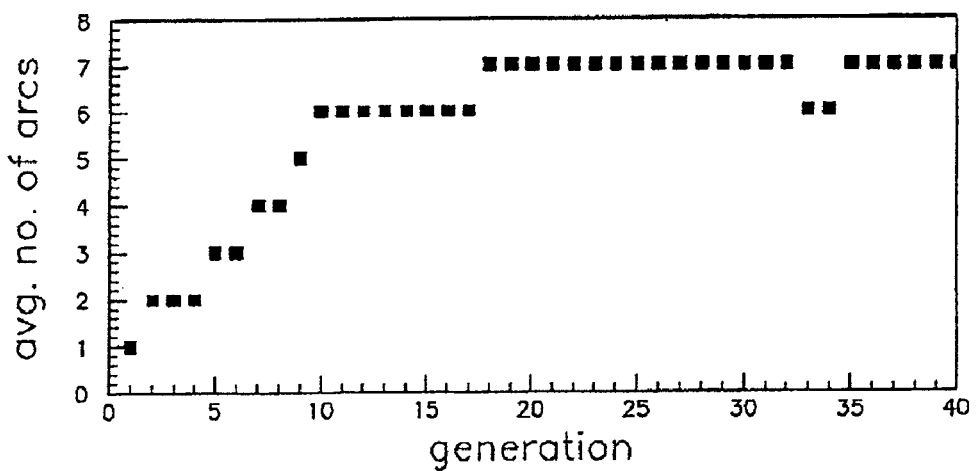
FIG. 5b shows the average number of arcs of the candidate networks as a function of the generation number.
Figure 6:
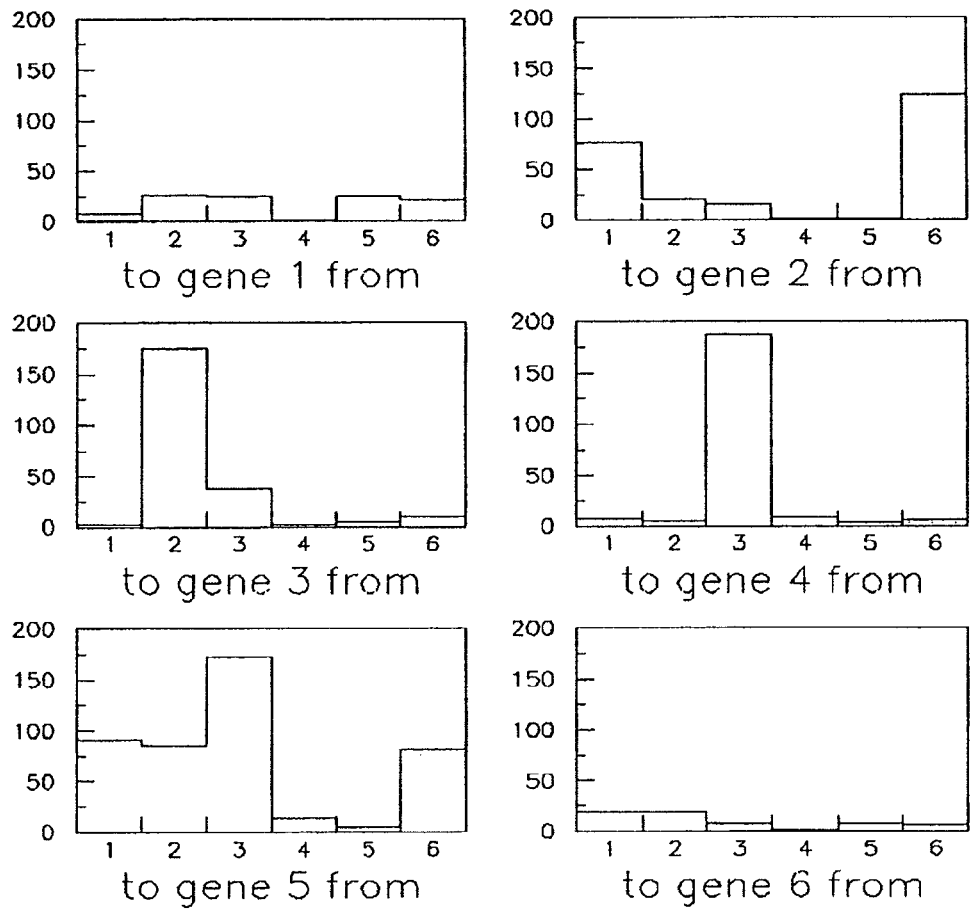
FIG. 6 shows the histograms of the arcs in the candidate networks at generation 25.

Note that the expression patterns of gene 1 and gene 6 are similar in that they are not regulated by others and their decay constants differ by a factor of 2. If the arc from gene 1 to gene 2 is replaced by an arc from gene 6 to gene 2 and the value of $\omega_{12}$ in Equation (6) is changed from 2.0 to 4.0, an identical dataset is obtained. That means the system cannot differentiate gene 1 from gene 6 and should thus return with equal chance different solutions (structures and parameters) that yield the same highest score. In this simulation, the implementation is run under a population size of 200 and quit while the average network score of the population stops climbing. FIG. 5a shows the increase in the average score as the iteration is conducted. FIG. 5a shows the average number of arcs of the candidate networks as a function of the generation number. From the figures, it is known that we can quit the program at generation 25. FIG. 6 shows the histograms of the arcs in the candidate networks at generation 25. In this figure, each column shows probabilities of the existence of an arc from gene numbered under the column to each corresponding gene. The top 5 tall columns give top 5 significant arcs which are proven to be the correct arcs from which the data were generated. Note that since gene 1 and gene 6 are indistinguishable, column 1 and column 6 in the upper right and lower left histograms of FIG. 6 are roughly of the same height (significance).

Application in Yeast Cell-Cycle Microarray Data

Before application to real biological data, the model of regulation in Equation (2) is extended to accommodate delayed transcription, as follows:

$$x_i(t+1) = \alpha_i \prod_j x_j(t)^{\omega_{ji}} \prod_k x_k(t-1)^{\omega_{ki}} \prod_l x_l(t-2)^{\omega_{li}} + (1-\beta_i)x_i(t) + \varepsilon \quad (7)$$

wherein expression of gene k at time point t−1 affects that of gene i at time point t+1, and so on. The number of allowable different time lags depends on the data. For example, in a time series experiment with only 7 time points, a maximum of 3 time lags may be allowed. The structural search space trebles in such case.

The methodology is applied to a standard time-series microarray dataset on the yeast *Saccharomyces cerevisiae* during cell cycle. The microarray experiment was performed by P. T. Spellman et al. and the data are available at the website: http://genome-www.stanford.edu/cellcycle/.

At different stages of a cell cycle, different sets of genes are activated with products performing vital cell-cycle dependent functions such as budding, DNA replication/repair, mitosis control, cytokinesis, and mating. Coordinate expression of the stage-specific genes during cell cycle is thus an important feature of the cell cycle regulation. To model the regulation, $x_i$ on the left-hand side of Equation (7) represents the expression ratios of those cell-cycle dependent genes (target genes) while $x_j$, $x_k$, $x_l$ on the right are those of the transcription factors. Establishment of an arc represents a regulation of a target gene by a transcription factor.

Among the four datasets available in the database, the "a factor" datasets, where genome-wide (7,220 ORF's) expressions were measured at 18 time points at an even time interval of 7 minutes, were chosen for analysis. The raw data are those provided at the above-said webpage. In the data file, the expression levels of a gene, including the background reading, at a time point are recorded in a row. The program reads in the expression ratios of interest. Since the time series spans roughly two cell cycles, 5 time lags on the right of Equation (7) were allowed. T hey are t, t−1, t−2, t−3 and t−4.

Figure 7:
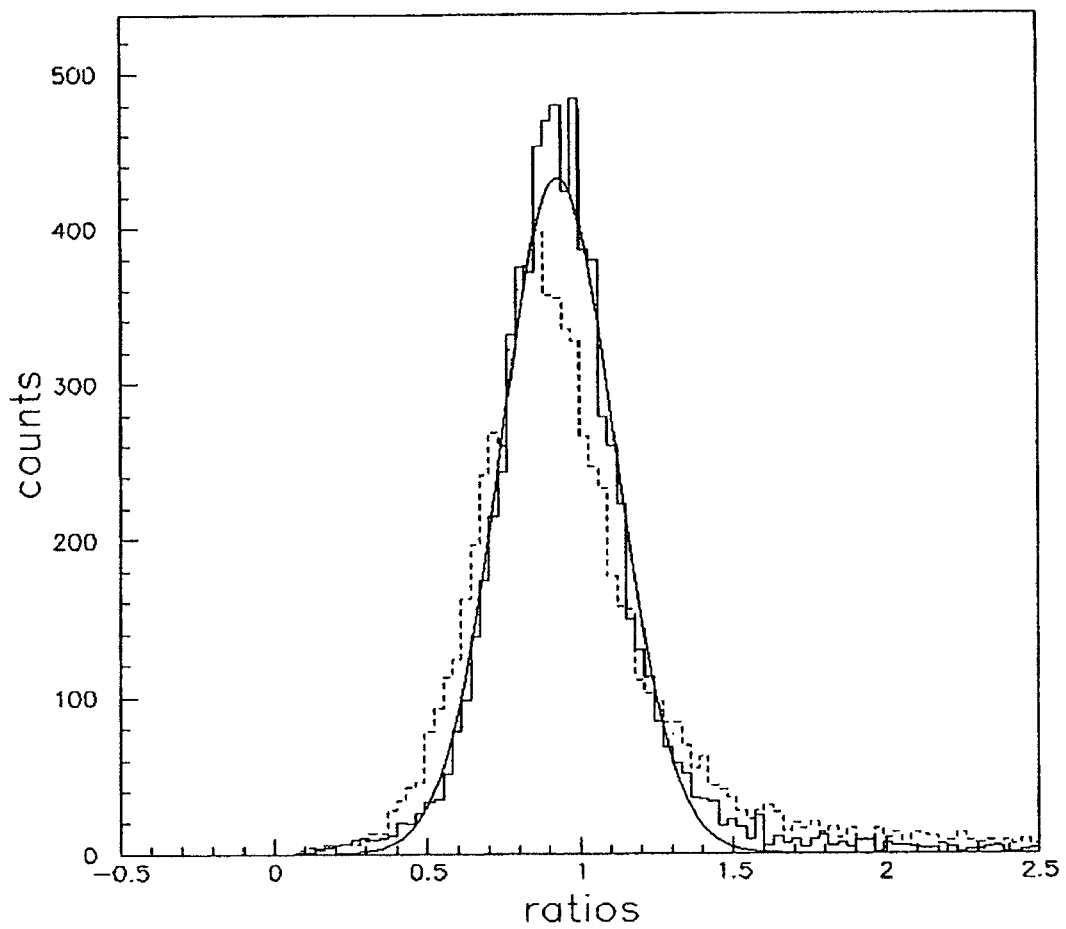
FIG. 7 shows the histogram of the 7,220 genome-wide expression ratios of the first time point of a dataset used in the embodiment of this invention, in comparison with a Gaussian.

The noise level of the measurement, i.e. δ of the Gaussian noise E in Equation (7), limits the resolution of the reconstruction. The genome-wide expression ratios measured at the first time point when the cells were just about to grow, were histogrammed. If there were no noise, the red to green rations would read one. FIG. 7 shows the histogram so obtained. In this figure, the solid line histogram is the 7,220 ratios in the dataset at the first time point. The smooth curve shows a Gaussian fit to it. The mean of the Gaussian is 0.93 and the standard deviation is 0.19 (δ=0.19). The dashed line histograms the 7,220 ratios at the second time point. Comparing the two histograms, it can be seen that some genes started their expression by the second time point.

Figure 8:
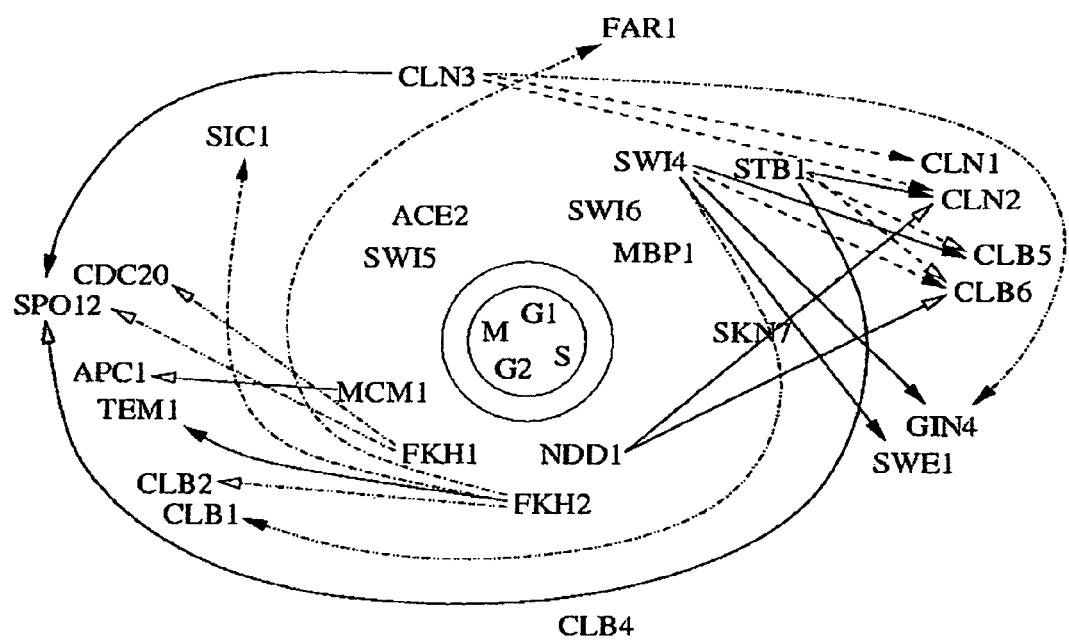
FIG. 8 shows a reconstructed yeast cell-cycle gene regulation network from time-series microarray data using the present invention.

At least 11 yeast transcription factors (SWI4, SWI6, STB1, MBP1, SKN7, NDD1, FKH1, FKH2, MCM1, SWI5, ACE2) and one cyclin gene (CLN3) are known to have the ability to activate cell-cycle dependent genes. Although about 800 genes showed periodic expression during a cell cycle, only few activators→target pairs are known in the prior art. In this embodiment, 15 target genes are selected: CLN1, CLN2, CLB5, CLB6, GIN4, SWE1, CLB4, CLB1, CLB2, TEM1, APC1, SPO12, CDC20, SIC1, FAR1, since their transcription activators are known. The methodology in this invention was applied to the real microarray data. The evolution in the computer program stops after the average score of the 3,600 networks in the GA population ceases to grow. FIG. 8 shows the significant arcs in the reconstructed regulation network. The program, written in Java, finishes in one hour on a 2.0 GHz PENTIUM® IV PC running REDHAT® 7.3 LINUX®. In FIG. 8, the solid, dashed, dotted, dotted dashed and dotted dotted dashed lines represent respectively influences of regulation from time pints t, t−1, t−2, t−3 and t−4. The sign of the ω's are positive (negative) for solid (empty) arrow heads.

To help assess the performance of the present invention, known facts are summarized here: MBF (a complex of MBP1 and SWI6) and SBF (a complex of SWI4 and SWI6) control late G1 genes. MCM1, together with FKH1 or FKH2, recruits the NDD1 protein in late G2 and controls the transcription of G2/M genes. SWI5 and ACE2 regulate genes at M/G1. Only 5 arcs (NDD1→CLN2, NDD1→CLB6, STB1→SPO12, CLN3→SPO12, and CLN3→GIN4) in the 22 reconstructed arcs in FIG. 8 are not accounted for by experiments to date.

In short, this analysis demonstrates that, when this invention is applied to microarray data of the yeast *Saccharomyces*

*cerevisiae* during cell cycle, the reconstructed regulation network, involving 27 genes, unveils 22 arcs, 17 of which are consistent with experimental findings.

EFFECTS OF THE INVENTION

The present invention disclosed a computation-oriented approach for reconstruction of gene networks from time series microarray data. This invention applies the method of Bayesian networks to reconstruct gene regulation networks from time series microarray data. A nonlinear function to model the change of gene expression levels over time is disclosed. Levels of gene expression are continuous in this invention. A scoring metric related to the probability density of the measured expression data is employed. Network reconstruction became an optimization problem where relations among genes are sought to maximize the score. A downhill simplex algorithm is implemented for parameter estimation and genetic algorithm for structure search. Operations that do not always grow structures in the generic algorithm are disclosed: arcs can be either added or removed from the networks to prevent data over-fitting. The invention is tested in simulation to find degenerate global optimal solutions. The ensemble of the networks in the last generation of the genetic algorithm helped provide an implementation for a confidence metric. Using this invention to reconstruct yeast cell cycle gene regulation from DNA microarray data showed encouraging results. The method for reconstruction of gene networks from time series microarray data is amendable to such imposition as the speculated scale-free network property.

The result of this invention showed a promising direction toward gene network reconstruction from time-ordered microarray data. Using the system for reconstruction of gene networks of this invention, over-simplified comparison may be avoided and high successful prediction rate can be achieved. The present invention requires no ad hoc parameters and thus is user-friendlier, as it may be anticipated that the prospective users of this invention are biologists who have little statistics/computation expertise.

As the present invention has been shown and described with reference to preferred embodiments thereof, those skilled in the art will recognize that the above and other changes may be made therein without departing from the spirit and scope of the invention.

What is claimed is:

1. A method for establishment of causal regulation network from time series data, comprising the following steps:

obtaining a time-series dataset comprising data obtained at a series of time points;

generating from a computer tool a first predetermined amount of causal regulation network templates as candidate networks, each candidate network structure being represented by an integer array for genetic algorithm operations;

fitting data of said dataset into said candidate networks by downhill simplex method;

calculating joint probability density (score) of said fitted candidate networks, S, according to the following equation, respectively:

$$\text{score}(S) = \log(P(x \mid S, \hat{\Theta})) - \frac{d}{2}\log(R \cdot n \cdot (T-1))$$

wherein score(S) approximates the logarithm of the joint probability density of a candidate network, S, and the parameters, $\hat{\Theta}$, represent the values of the parameters $\Theta$ that maximize the likelihood function P(x|S,$\Theta$), wherein:

$$P(x \mid S, \Theta) = \prod_{t=1}^{T-1} \prod_{i=1}^{n} p(x_i, t; \theta_i),$$

wherein $p(x_i, t; \theta_i)$ represents conditional probability density of datum i in said candidate network at time t, relatively to parameters $\theta_i$, $\Theta$ is the cell containing parameters $\theta_i$, n represents number of data included in said candidate networks and T represents number of time points, and $x_i$ is the value of datum i and is non-negative real; wherein:

$$p(x_i, t+1; \theta_i) = N\left(x_i(t+1) - \alpha_i \prod_j x_j(t)^{\omega_{ji}} - (1-\beta_i)x_i(t), \delta^2\right)$$

wherein exponent, $\omega_{ji}$, is real, wherein, when $\omega_{ji}$ is positive (negative), datum j induces (represses) the value of datum i and, $\alpha_i$ and $\beta_i$ are both positive constants, quantifying the rate of induction and repression, respectively, $$x_i(t+1) = \alpha_i \prod_j x_j(t)^{\omega_{ji}} + (1-\beta_i)x_i(t) + \varepsilon_i(t)$$

wherein $\varepsilon_i(t)$ is the measurement error for datum i at time t, $\delta^2$ is variance of distribution in a Gaussian distribution representing said errors, $\varepsilon_i(t)$; and $$\frac{d}{2}\log(R \cdot n \cdot (T-1))$$

is a penalty against structure complexity, d equals to the number of parameters in said candidate network, n represents number of data included in said fitted candidate networks, T represents number of time points 0, 1, 2, . . . , T−1, and R represents number of repeats of said measurement;

selecting from said fitted candidate networks a second predetermined number of candidate networks with the highest score values;

mating and mutating said selected candidate networks according to the genetic algorithm to generate offspring candidate networks;

fitting data of said dataset into said offspring networks and calculating score values of said offspring networks;

determining whether the average of the obtained score values reaches a plateau;

if not, repeating steps of said mating and mutating and said score calculation;

otherwise, selecting a third predetermined number of the offspring candidate networks with highest score values; and outputting said selected offspring candidate networks as result of establishment of causal regulation network.

2. The method for establishing causal regulation network from time series data according to claim 1, further comprising, after selecting said third predetermined number of offspring candidate networks with highest score values, the steps of:

calculating the frequency of existence of arcs in said selected offspring candidate networks;

ranking arcs according to existence frequencies and selecting arcs of existence frequency values greater than a user-definable threshold value;

reconstructing causal regulation network using said selected arcs and related values of data; and outputting result of said reconstruction.

3. The method for establishment of causal regulation network from time series data according to claim 1 or 2, wherein said candidate networks comprise network structures under the genetic algorithm and are expressed by arrays of integers.

4. The method for establishment of causal regulation network from time series data according to claim 1 or 2, wherein said time series data comprise gene expression microarray data.

5. A method for reconstruction of gene networks from time series microarray data, comprising the following steps:

obtaining a time-series microarray dataset of gene expression relating to a set of genes and their related materials;

generating from a computer tool a first predetermined amount of gene regulation network templates as candidate networks, each candidate network structure being represented by an integer array for genetic algorithm operations;

fitting data of said dataset into said candidate networks by downhill simplex method;

calculating joint probability density (score) of said fitted candidate networks, S, according to the following equation, respectively:

$$\text{score}(S) = \log(P(x \mid S, \hat{\Theta})) - \frac{d}{2}\log(R \cdot n \cdot (T-1))$$

wherein score(S) approximates the logarithm of the joint probability density of a candidate network, S, and the parameters, $\hat{\Theta}$, represent the values of the parameters $\Theta$ that maximize the likelihood function $P(x|S, \Theta)$, wherein:

$$P(x \mid S, \Theta) = \prod_{t=1}^{T-1} \prod_{i=1}^{n} p(x_i, t; \theta_i),$$

wherein $p(x_i, t; \theta_i)$ represents conditional probability density of the expression of any gene i in said candidate network at time t, relatively to parameters $\theta_i$, and $\Theta$ is the cell containing parameters $\theta_i$, and $x_i$ is the measured expression ratio of gene i and is non-negative real; wherein:

$$p(x_i, t+1; \theta_i) = N\left(x_i(t+1) - \alpha_i \prod_j x_j(t)^{\omega_{ji}} - (1-\beta_i)x_i(t), \delta^2\right)$$

wherein exponent, $\omega_{ji}$, is real, wherein, when $\omega_{ji}$ is positive (negative), gene j induces (represses) the expression of gene i and, $\alpha_i$ and $\beta_i$ are both positive constants, quantifying the rate of induction and repression, respectively, $$x_i(t+1) = \alpha_i \prod_j x_j(t)^{\omega_{ji}} + (1-\beta_i)x_i(t) + \varepsilon_i(t)$$

wherein $\varepsilon_i(t)$ is the measurement error for gene i at time t, $\delta^2$ is variance of distribution in a Gaussian distribution representing said errors, $\varepsilon_i(t)$; and $$\frac{d}{2}\log(R \cdot n \cdot (T-1))$$

is a penalty against structure complexity, d equals to the number of parameters in said candidate network, n represents number of genes included in said candidate networks and T represents number of microarray measurements performed at time points 0, 1, ..., T−1, and R represents number of repeats of said measurement;

selecting from said fitted candidate networks a second predetermined number of candidate networks with the highest score values;

mating and mutating said selected candidate networks according to the genetic algorithm to generate offspring candidate networks;

fitting data of said dataset into said offspring candidate networks and calculating score values of said offspring networks;

determining whether the average of the obtained score values reaches a plateau;

if not, repeating steps of said mating and mutating and said score calculation;

otherwise, selecting a third predetermined number of the offspring candidate networks with highest score values; and outputting said selected offspring candidate networks as result of construction of gene network.

6. The method for reconstruction of gene network from time series data according to claim 5, further comprising, after selecting said third predetermined number of offspring candidate networks with highest score values, the steps of:

calculating the frequency of existence of arcs in said selected offspring candidate networks;

ranking arcs according to existence frequencies and selecting arcs of existence frequency values greater than a user-definable threshold value;

reconstructing gene network using said selected arcs and related genes and related materials; and outputting result of said reconstruction.

7. The method for reconstruction of gene networks from time series data according to claim 5 or 6, wherein said candidate networks comprise network structures under the genetic algorithm and are expressed by arrays of integers.

\* \* \* \* \*